(12) United States Patent
Vij

(10) Patent No.: US 8,548,547 B2
(45) Date of Patent: Oct. 1, 2013

(54) AVIATION PHYSIOLOGICAL HEALTH MONITORING SYSTEM AND METHOD

(76) Inventor: Ashok K. Vij, Tucson, AZ (US)

( * ) Notice: Subject to any disclaimer, the term of this patent is extended or adjusted under 35 U.S.C. 154(b) by 0 days.

(21) Appl. No.: 12/803,555

(22) Filed: Jun. 29, 2010

(65) Prior Publication Data

US 2011/0040156 A1    Feb. 17, 2011

Related U.S. Application Data

(60) Provisional application No. 61/221,488, filed on Jun. 29, 2009.

(51) Int. Cl.
*A61B 6/00* (2006.01)
(52) U.S. Cl.
USPC .......................................................... 600/323
(58) Field of Classification Search
USPC .......................................................... 600/323
See application file for complete search history.

(56) References Cited

U.S. PATENT DOCUMENTS

| 7,246,620 | B2 * | 7/2007 | Conroy, Jr. ............... | 128/205.11 |
| 2004/0193068 | A1 * | 9/2004 | Burton et al. ................ | 600/544 |
| 2007/0043482 | A1 * | 2/2007 | Aimar .............................. | 701/4 |
| 2007/0120693 | A1 * | 5/2007 | Vij .................................. | 340/632 |
| 2008/0146892 | A1 * | 6/2008 | LeBoeuf et al. .............. | 600/300 |
| 2010/0225493 | A1 * | 9/2010 | Zishaan ........................ | 340/627 |

* cited by examiner

*Primary Examiner* — Clayton E Laballe
*Assistant Examiner* — Warren K Fenwick

(57) ABSTRACT

An aircraft cockpit with health monitoring system and method enables an occupant (e.g. a pilot) and/or a ground station to monitor the physical condition of the occupant during a flight. A sensor such as a pulse oximetry sensor is in predetermined location to an occupant seat (e.g. an aircraft cockpit seat), within the field of reach of a person seated in the seat. The sensor is supported in the predetermined location in a stable manner that provides sufficient reaction to insertion of a finger to enable insertion of a finger in the sensor while the person is in a seated position, and the sensor is in communication with a control box that processes data from the sensor, and presents the data, e.g. at a the multi functional display in an aircraft cockpit. During a flight, a pilot seated in the aircraft cockpit seat will be prompted to insert a finger into the pulse oximetry sensor to produce output at the multi functional display.

17 Claims, 11 Drawing Sheets

AVIATION PHYSIOLOGICAL HEALTH MONITORING SYSTEM AND METHOD

RELATED APPLICATION/CLAIM OF PRIORITY

This application is related to and claims priority from provisional application Ser. No. 61/221,488 filed Jun. 29, 2009, which provisional application is incorporated by reference herein.

INTRODUCTION AND SUMMARY OF THE PRESENT INVENTION

The present invention relates to a health monitoring system and method that is designed for an aircraft and functions to enable an occupant such as a pilot, and/or a real time ground station to monitor the physiological condition the occupant.

The health monitoring system can comprise of any one of pulse oximetry, heart rate, blood pressure, body temperature, glucose level (blood sugar), alcohol detection system breath analyzer and any other health related vital signs of interest in aircraft cabin.

The present invention is particularly designed to minimize the risk of a pilot suffering hypoxia that can be dangerous to the pilot as well as the aircraft and its occupants. Hypoxia is a pathological condition in which the body as a whole (generalized hypoxia) or a region of the body (tissue hypoxia) is deprived of adequate oxygen supply. Generalized hypoxia occurs in healthy people when they ascend to high altitude, where it causes altitude sickness leading to potentially dangerous complications: high altitude pulmonary edema (HAPE) and high altitude cerebral edema (HACE). Hypoxia also occurs in healthy individuals when breathing mixtures of gases with a low oxygen. At night, the risk is even higher, because human eyes have a harder time distinguishing colors and have diminished resolution, but have a much higher sensitivity to light than the cones. Thus, at night a human generally needs higher blood oxygen so the lights are focused correctly. During flight a pilot work load is tremendous and if the pilot is not careful about his phylogial condition, he may inadvertently go into Hypoxia due to Altitude and stress. The present invention specifically addresses this problem by measuring the aircraft altitude via a built in pressure sensor and prompting the pilot to check himself periodically, based on the sensed altitude of the aircraft and time at that sensed altitude. As an example, a currently preferred version of the invention provides prompts to the pilot to check his pulse oximetry at the following altitudes and times, to minimize the risk of the pilot suffering hypoxia:

1) 5,000 feet at night (Dawn to Dusk) every 60 minutes
2) 10,000 feet every 60 minutes during the day
3) 12,500 to 15,000 every 30 minutes
4) 17,000 feet every 20 minutes
5) 20,000 feet every 15 minutes
6 25,000 Feet every 10 minutes The system comprises of a health monitoring sensor and a control box. The sensor could be tactile or non-contact type. The control box receives the data from the sensor, analyzes the data and transmits to any system of choice. A preferred system to which the data is transmitted to is a multi functional display. As an example, a pulse oximetry sensor is supported in the predetermined location in a stable manner that provides sufficient reaction to insertion of a finger of an occupant to enable insertion of a finger in the sensor while the person is in a seated position, and the sensor is in circuit communication with the multi functional display.

During a flight, a pilot seated in the aircraft cockpit seat inserts a finger into the pulse oximetry sensor produces output and transmit data to the control box.

The control box receives data via commonly used aircraft communication languages (RS232, Airinc 429 . . . ETC) or via Bluetooth or other wireless data standards.

During a flight the control box communicates with the cockpit Multi Function Display, to display the vital signs it has received on the cockpit Multi Function Display, in real time. Furthermore data can be stored in the control box, in the Multi Function Display system storage device for history analysis, or data can be transmitted in real time to a Ground Station for monitoring.

The invention is further described in the following detailed description and accompanying drawings and exhibits.

Figure 1:
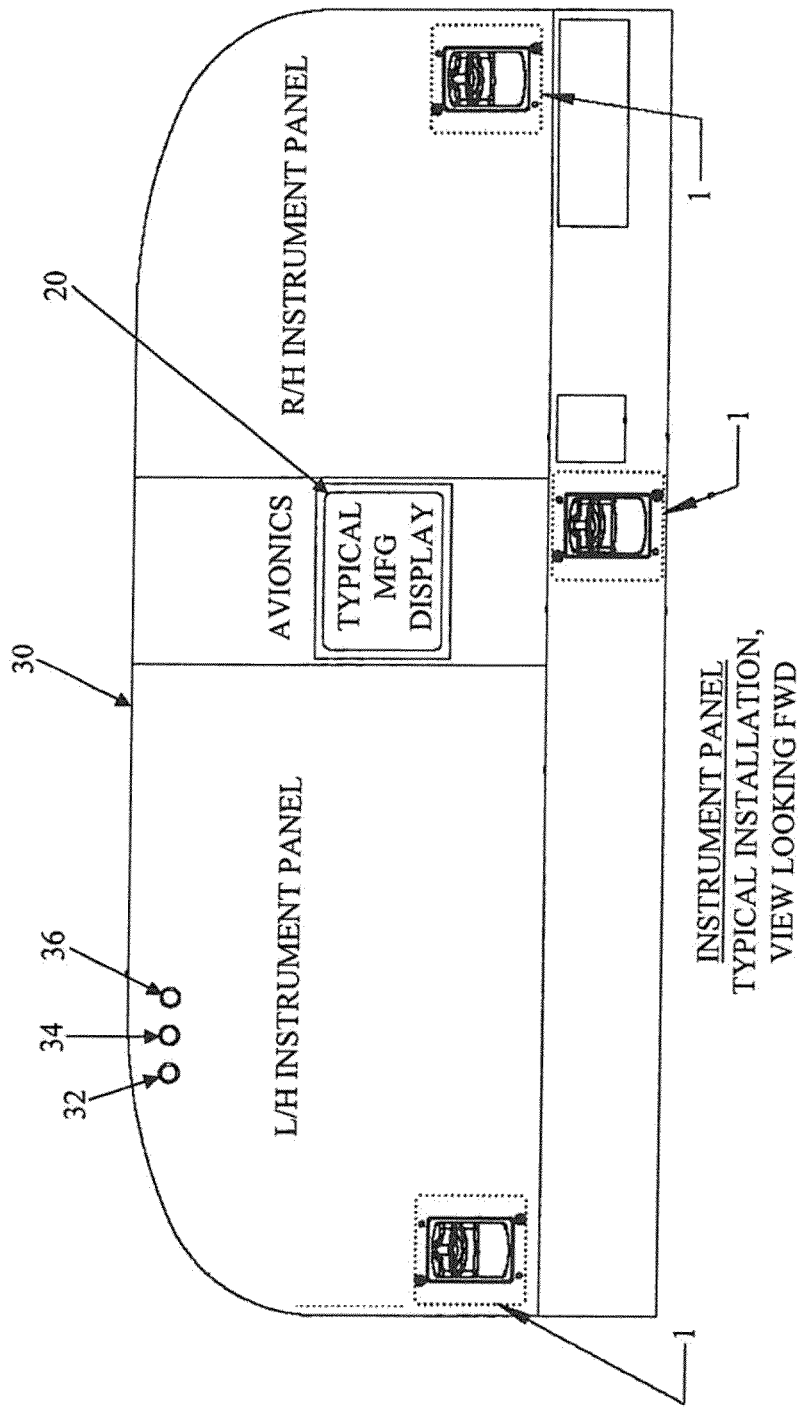
FIG. 1 is a schematic front view of an aircraft instrument panel with a plurality of pulse oximetry sensors, and multifunctional display, for a system and method in accordance with the principles of the present invention.

Exhibit B is an illustration of a multifunctional display of an aircraft, showing a "caution" signal produced at the display in accordance with the principles of the present invention;

Exhibit C is another illustration of a multifunction display of an aircraft, showing pilot vital information produced and highlighted at the display, in accordance with the principles of the present invention;

Exhibit D shows pulse oximetry sensors that are useful in a system and method according to the principles of the present invention; and Exhibit E is a detailed, exploded assembly view of the pulse oximetry sensor for a system and method according to the principles of the present invention, showing the relative locations of an altitude sensor, processor and CO sensor for a system and method according to the present invention.

DETAILED DESCRIPTION

As described above, the present invention relates to a health monitoring system and method that is designed for an aircraft and functions to enable an occupant such as a pilot, and/or a real time ground station to monitor the physiological condition the occupant.

The principles of the present invention are described in more detail herein, in connection with a system and method with a pulse oximetry sensor for an aircraft.

As a general overview, the present invention provides a system and method by which human vital condition data of a cockpit occupant (e.g. an aircraft pilot) is monitored, and output related to that condition is presented to the pilot (e.g. via the multifunctional display of the aircraft). A sensor (e.g. a pulse oximetry sensor) is configured to provide data related to at least one human vital condition, and is located within the reach of an occupant of the cockpit. The sensor is in communication with a processor for data from the sensor, and the processor provides the multi functional display with output related to the human vital condition based on the data from the sensor.

The sensor and the multifunctional display communicate, e.g. via a control box system, and the communication can be e.g. a wired connection, a wireless connection, etc. The sensor data is transmitted and/or recorded on the aircraft (aircraft black box or the control box system) or at a ground station.

The sensor is supported by one of an aircraft panel and seat, in stabilized condition in an aircraft panel, within reach of an occupant of the cockpit.

During operation of an aircraft, a person seated in the aircraft cockpit seat is prompted to engage the sensor to produce data as to the human vital condition of the occupant, that is communicated to the processor, and produces output at the multi functional display related to the human vital condition. Thus, if the occupant's vital signs require some attention by the occupant or others on the aircraft, the output at the multifunctional display is designed to get the attention of the occupant or such others. Preferably, an aircraft pilot will get periodic reminders based on the sensed altitude of the aircraft and time at the sensed altitude to monitor the pilot's vitals, and those periodic reminders will be shorter in time as the aircraft altitude increases. Thus, a pilot who is occupied with a myriad of tasks to perform in flying the aircraft, and who may otherwise be too busy to remind himself/herself to monitor vitals will be periodically prompted to monitor vitals, at an increasing frequency as the altitude of the aircraft increases.

The data from the sensor is also communicated to a storage device (e.g. the aircraft black box), so there is a continuing record of whether the pilot monitored his/her vitals as instructed, and if so what those vitals were when they were monitored. Also, such data may be communicated to a ground station, so that the pilot's vitals can be monitored at the ground station.

The data from the sensor is preferably blood oxygen data, but can also be related to any or all of the following additional human vital conditions: blood alcohol, blood glucose, body temperature, blood pressure. In addition, the system and method of monitoring pilot vitals is preferably combined with CO data produced by a system such as disclosed in applicant's U.S. patent application Ser. No. 11/288,716 (published application U.S. 2007/0120693 A1), which is incorporated by reference herein. Since CO levels can be at dangerous levels even before the pilot's vitals (e.g. blood oxygen will reflect the effect of the CO levels, the system and method are designed such that if CO levels reach a predetermined level an alert signal will be triggered, irrespective of the human vital condition that is being monitored.

Referring to the Figures and Exhibits, one or more pulse oximetry sensors 1 are located in an aircraft cockpit panel 30, in a predetermined relation to an aircraft cockpit seat 21. A multi functional display 20 is in predetermined location to the aircraft cockpit seat, within the field of view and within the reach of a person seated in the aircraft cockpit seat. The Multifunction display 20 is located in the cockpit panel, and displays information for the crew to navigate and operate the aircraft including monitoring of various aircraft systems. The multifunctional Display 20 can be part of the aircraft panel 30, which can be of a type produced, e.g. by manufacturers such as Garmin (Olathe Kans.), Honeywell (Phoenix, Ariz.), Rockwell Collins (Cedar Rapids, Iowa). The sensors 1 are preferably located in the aircraft panel 30, which would typically comprise a front panel, side panels, overhead and center and or side consoles.

Figure 2:
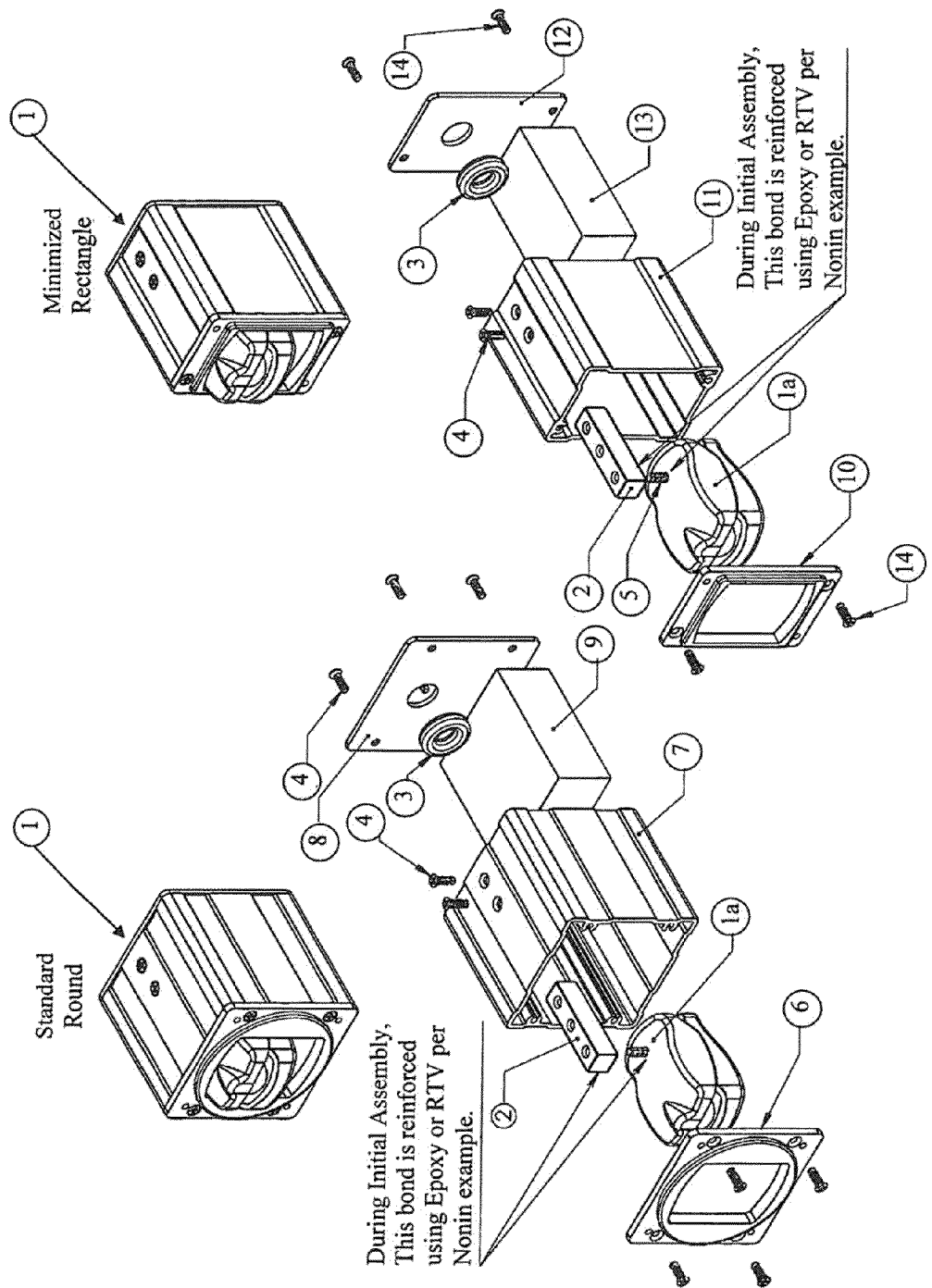
FIG. 2 is a series of exploded, assembly views of two versions of a pulse oximetry sensor for a system and method according to the principles of the present invention.
Figure 3:
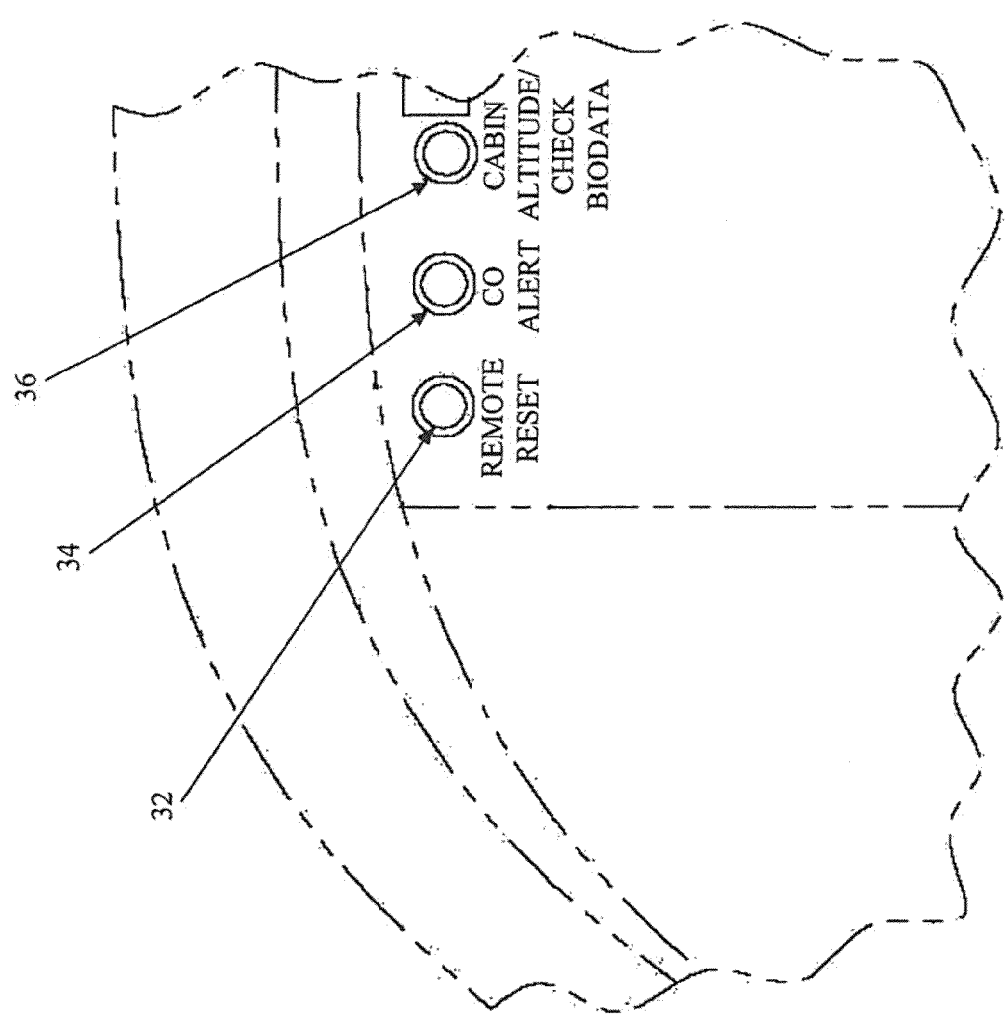
FIG. 3 is an enlarged view of a portion of the instrument panel of FIG. 1.
Figure 4:
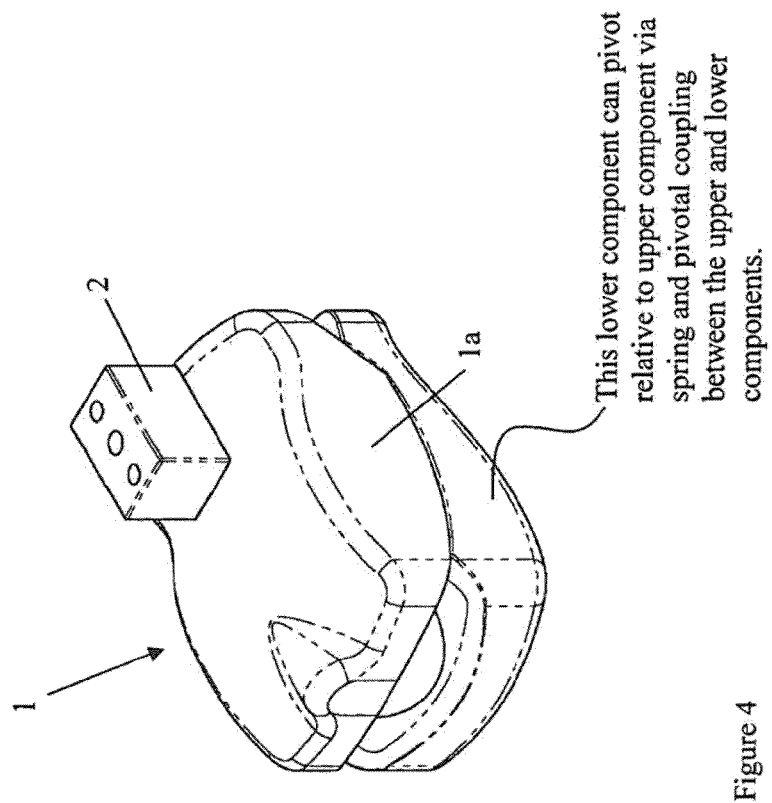
FIG. 4 is an exploded and partially assembled view of a pulse oximetry sensor for a system and method according to the principles of the present invention.
Figure 4:
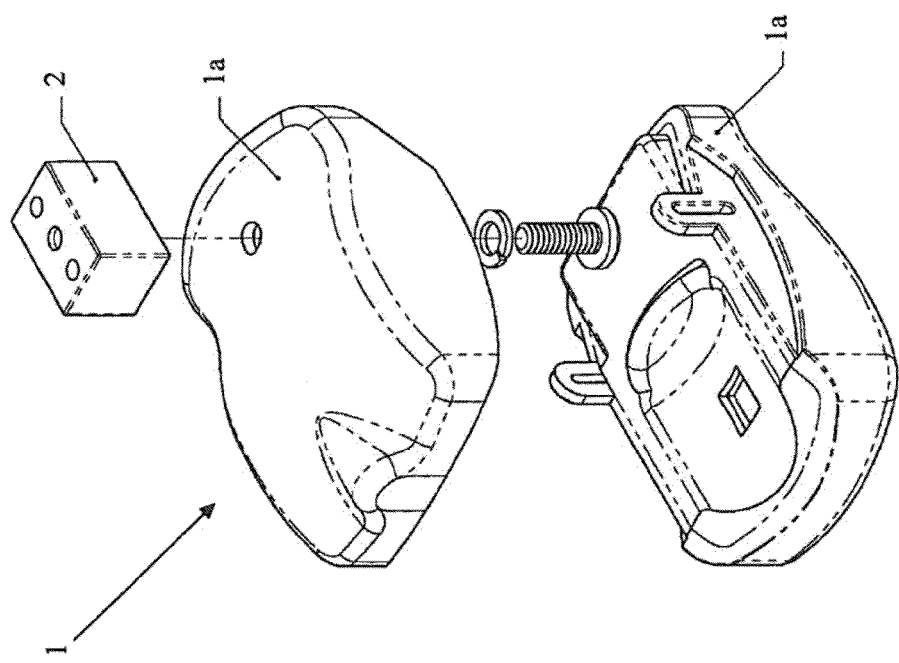
Figure 5:
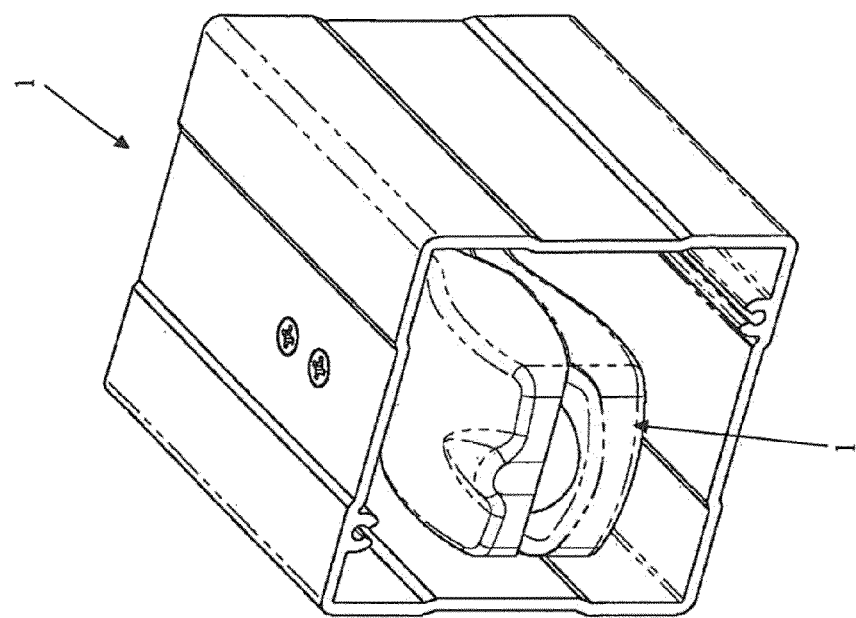
FIG. 5 is another exploded and partially assembled view of a pulse oximetry sensor for a system and method according to the principles of the present invention.
Figure 5:
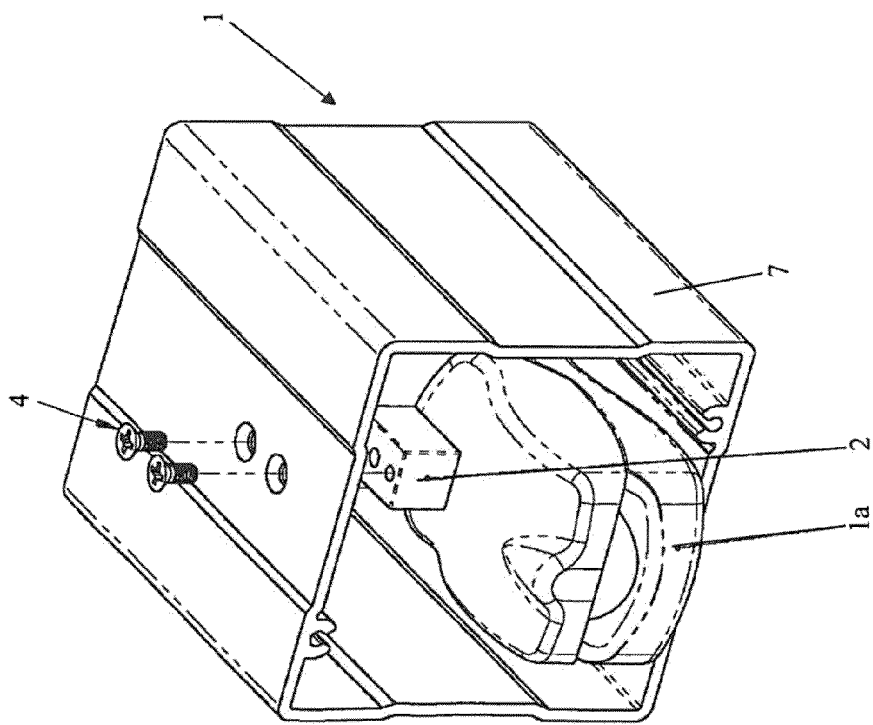

FIG. 2 shows two versions a pulse oximetry sensor 1, for a system and method according to the present invention. One version is referred to as "round" and the other version is referred to as "rectangular", depending on the configuration of the face plate of the pulse oximetry sensor 1.

In each version of the pulse oximetry sensor 1 shown in FIG. 2, a pulse oximetry component 1a has a pair of jaws that can pivot relative to each other to enable insertion of a person's finger. The actual structure of the pulse oximetry sensor component 1a is essentially the same as a pulse oximetry component that is typically found in a medical environment (e.g. in an operating room). In a medical environment a medical person manually manipulates the sensor component to open the pair of jaws so that a finger can be inserted into the jaws. In a pulse oximetry sensor 1 for the present invention, a housing is provided (parts 7, 11) and the sensor component 1a is stabilized in the housing (e.g. by a universal mount 2, grommet 3, screws 4, threaded head 5, backing plates 8, 12, and foam backings 9, 13), with the upper jaw of the pulse oximetry component 1a fixed to the housing, and the lower jaw coupled to the upper jaw via a pivotal connection and a biasing spring that allows the lower jaw to pivot relative to the upper jaw. The face plates (6, 10) of the pulse oximetry sensor are located so that a person can insert a finger into the pulse oximetry sensor 1 through the face plate.

When one or more the pulse oximetry sensors 1 is located in an aircraft cockpit panel 30, the sensor is located so that jaws of the sensor are accessible to a person seated in the cockpit (see Exhibit A, showing the sensor 1 located is an aircraft cockpit panel 30, within reach of a person seated in a seat 21 of the cockpit). The upper jaw of the sensor 1 is stabilized in a manner that provides a reaction force to a person sticking a finger into the sensor. Thus, when the sensor 1 is fixed in position in a cockpit, the upper jaw of the sensor is effectively fixed in position in the cockpit, and when a person sticks a finger into the jaws of the sensor 1, the lower jaw will pivot downward to enable the proper insertion of the finger.

Figure 6:
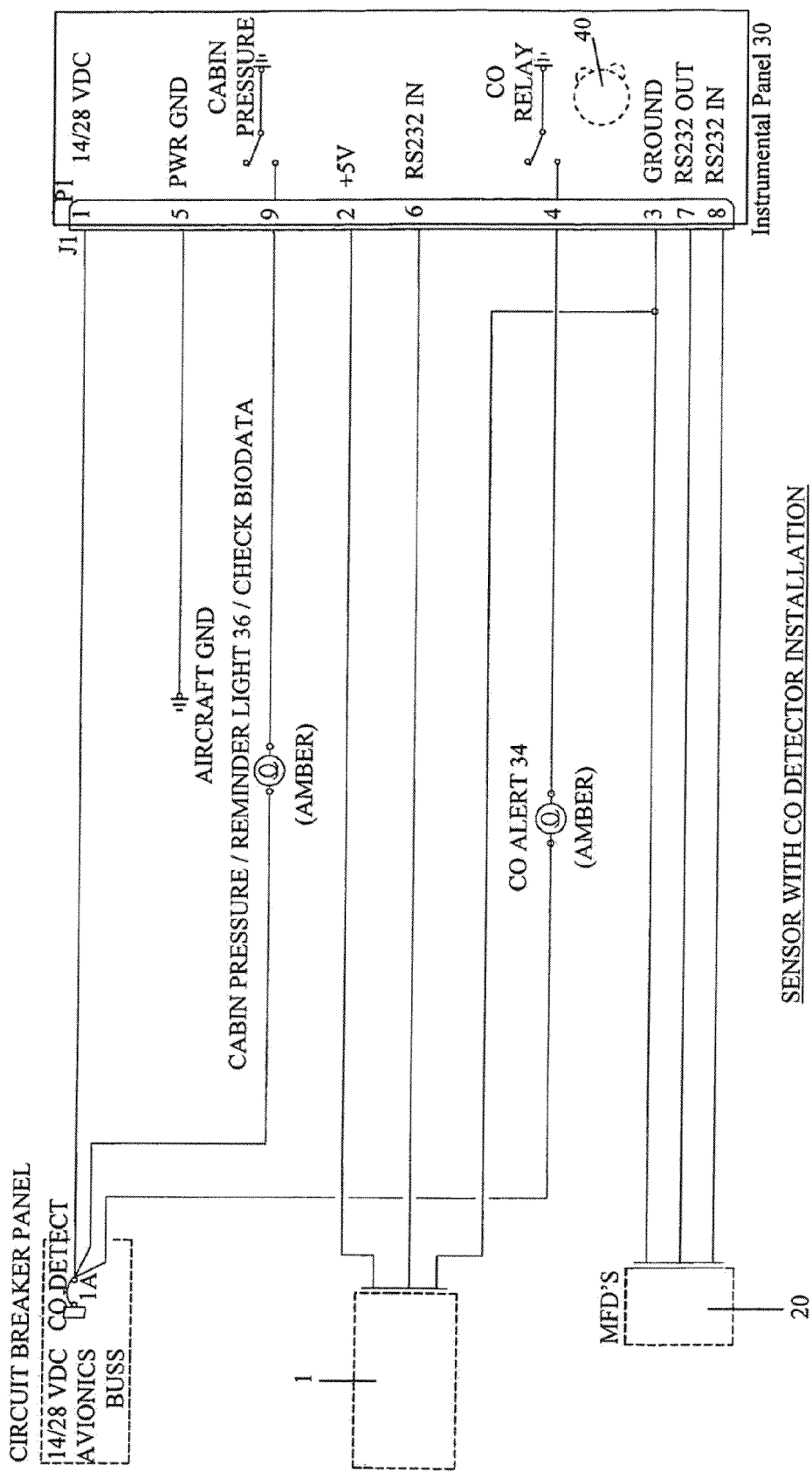
FIG. 6 is a wiring diagram for establishing circuit communication between a pulse oximetry sensor and control box, in a system and method according to the present invention Exhibit A is an illustration of an aircraft cockpit, showing one location for a pulse oximetry sensor for a system and method according to the present invention.
Figure 7:
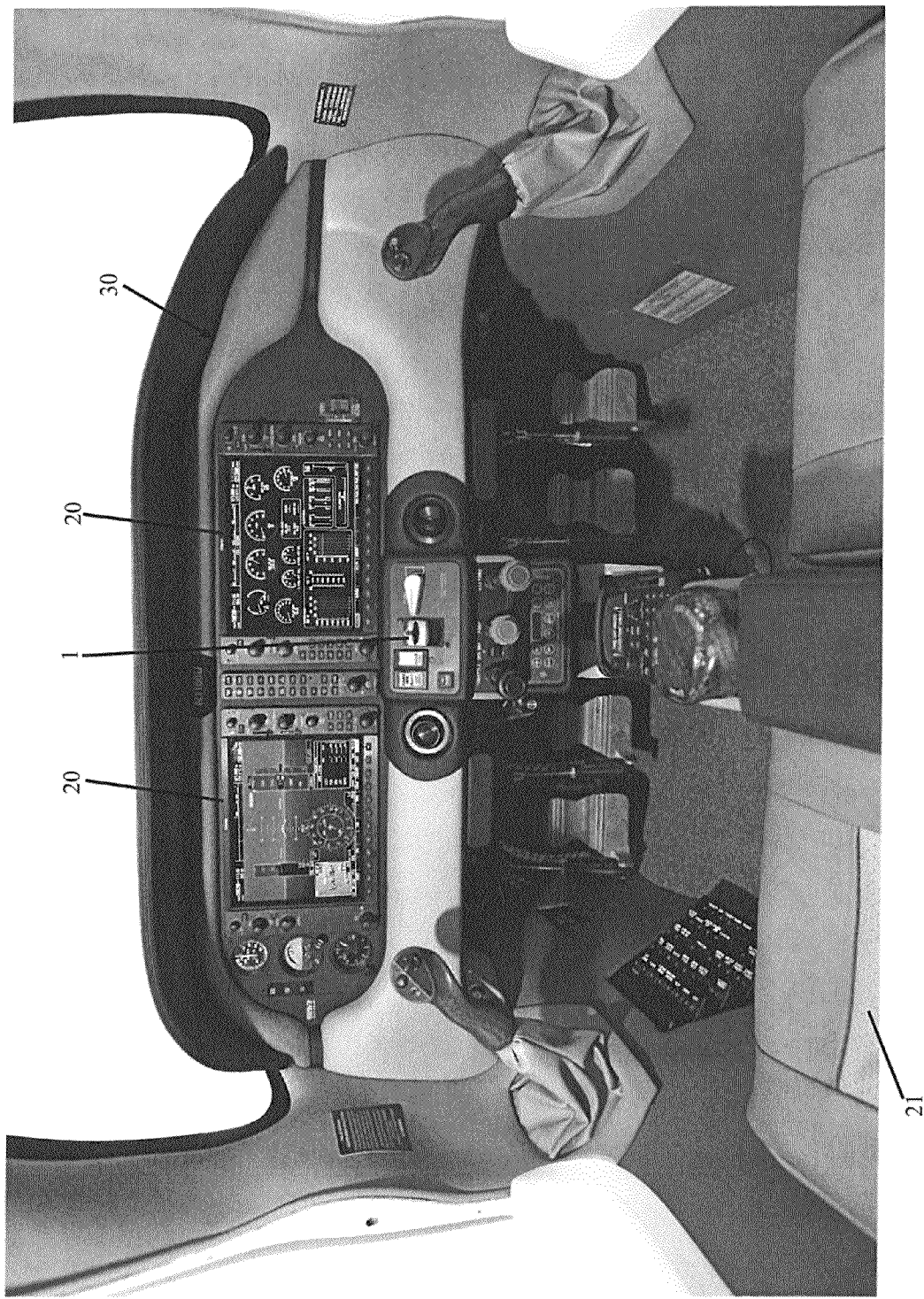
Figure 8:
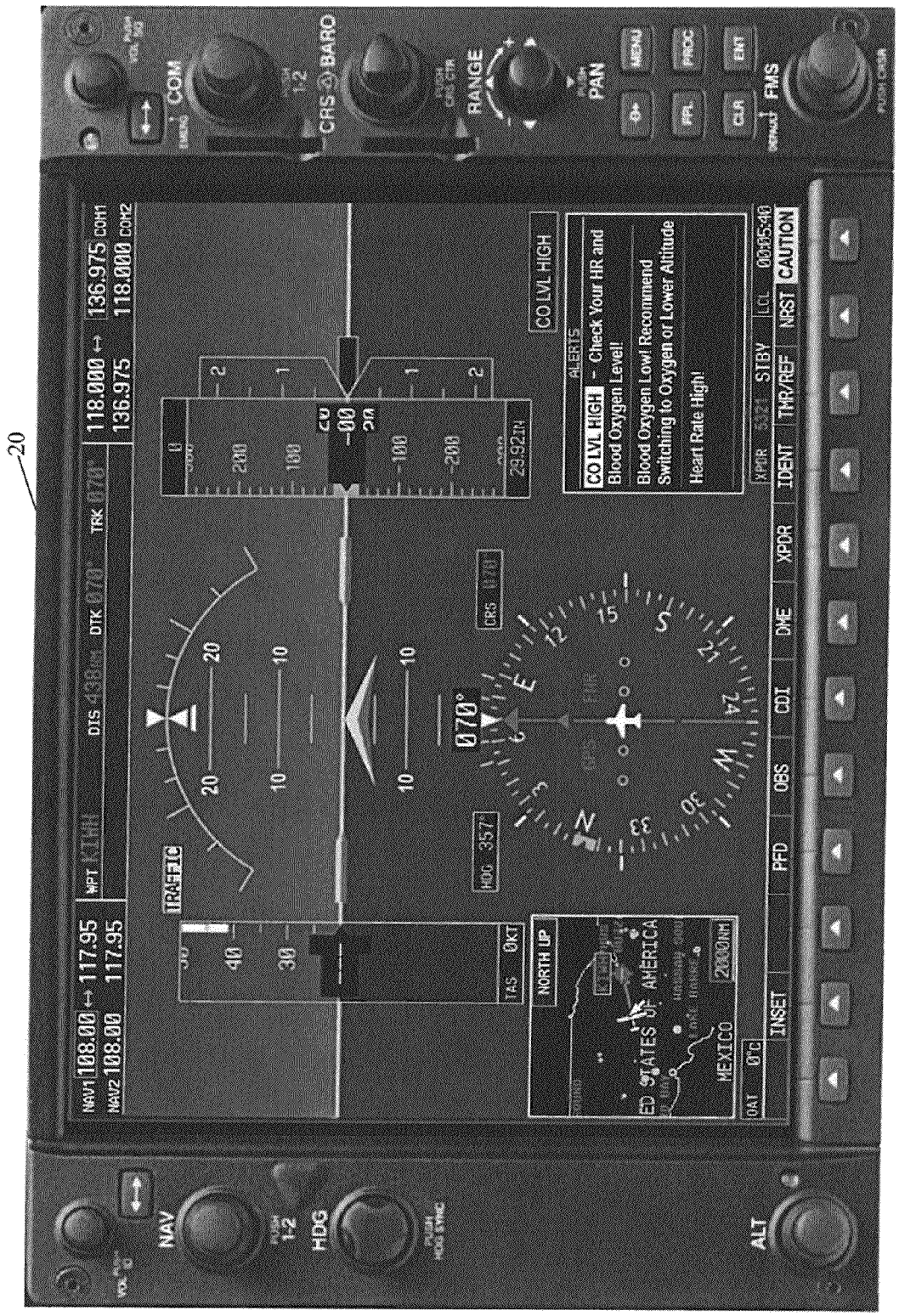
Figure 9:
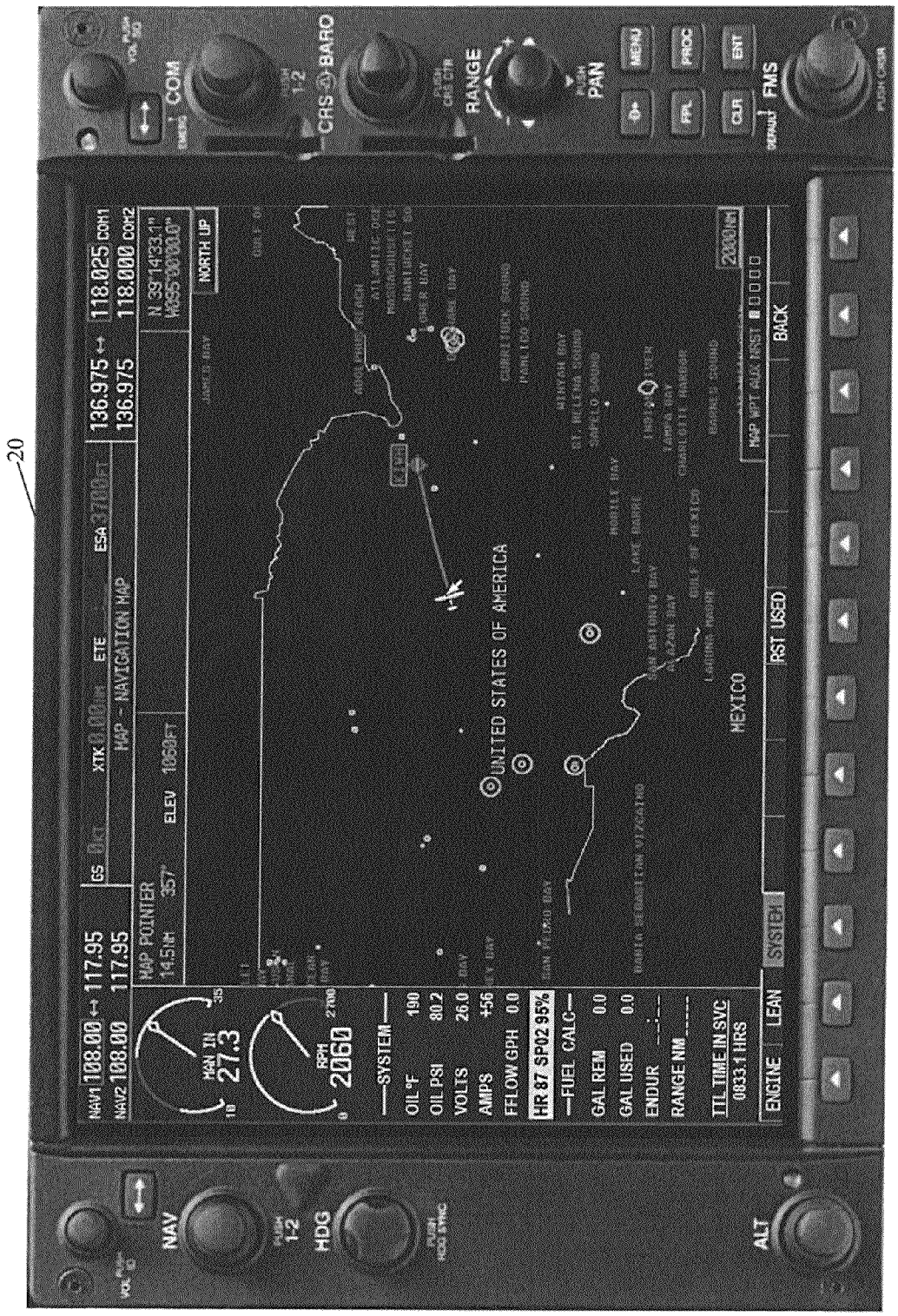
Figure 10:
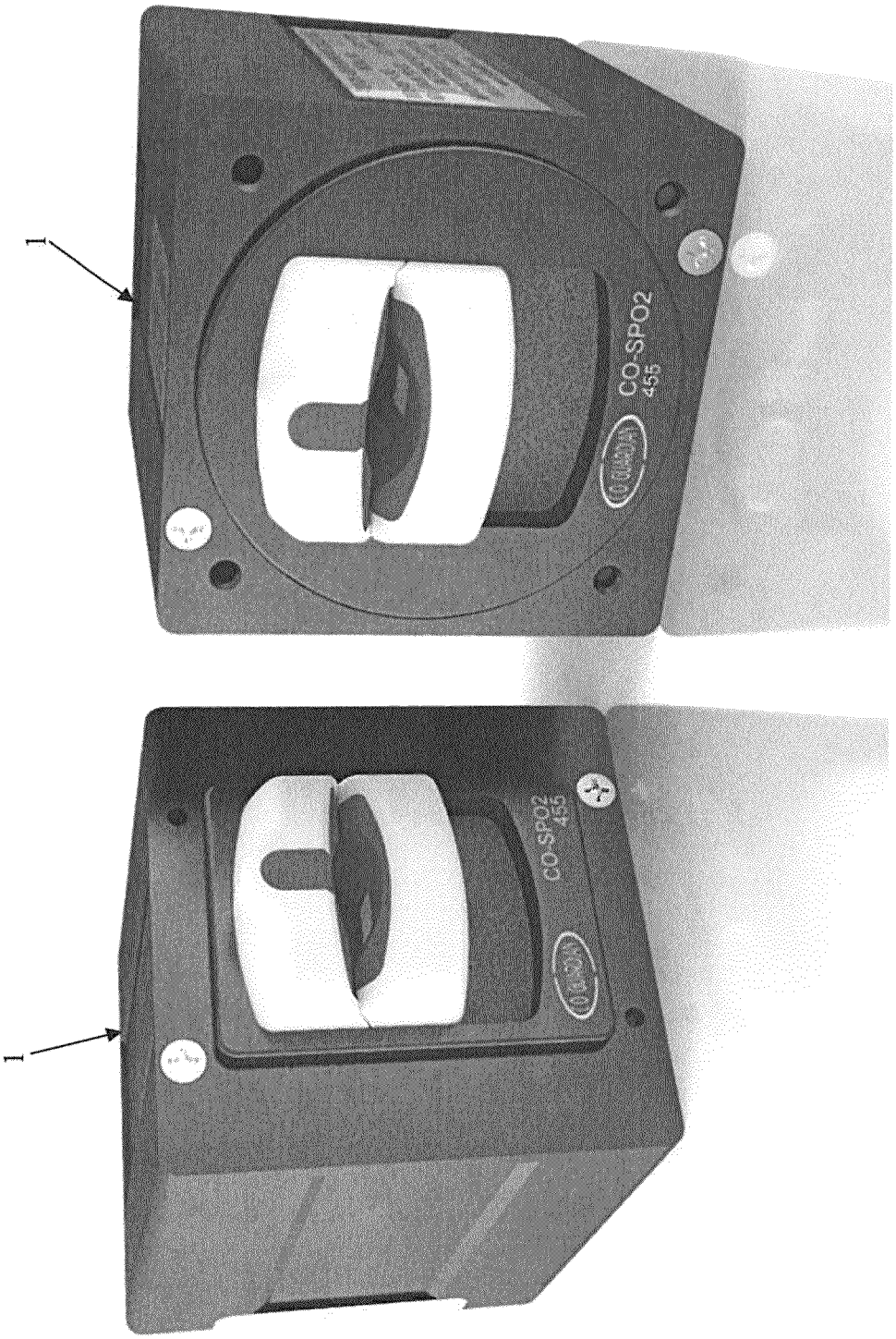
Figure 11:
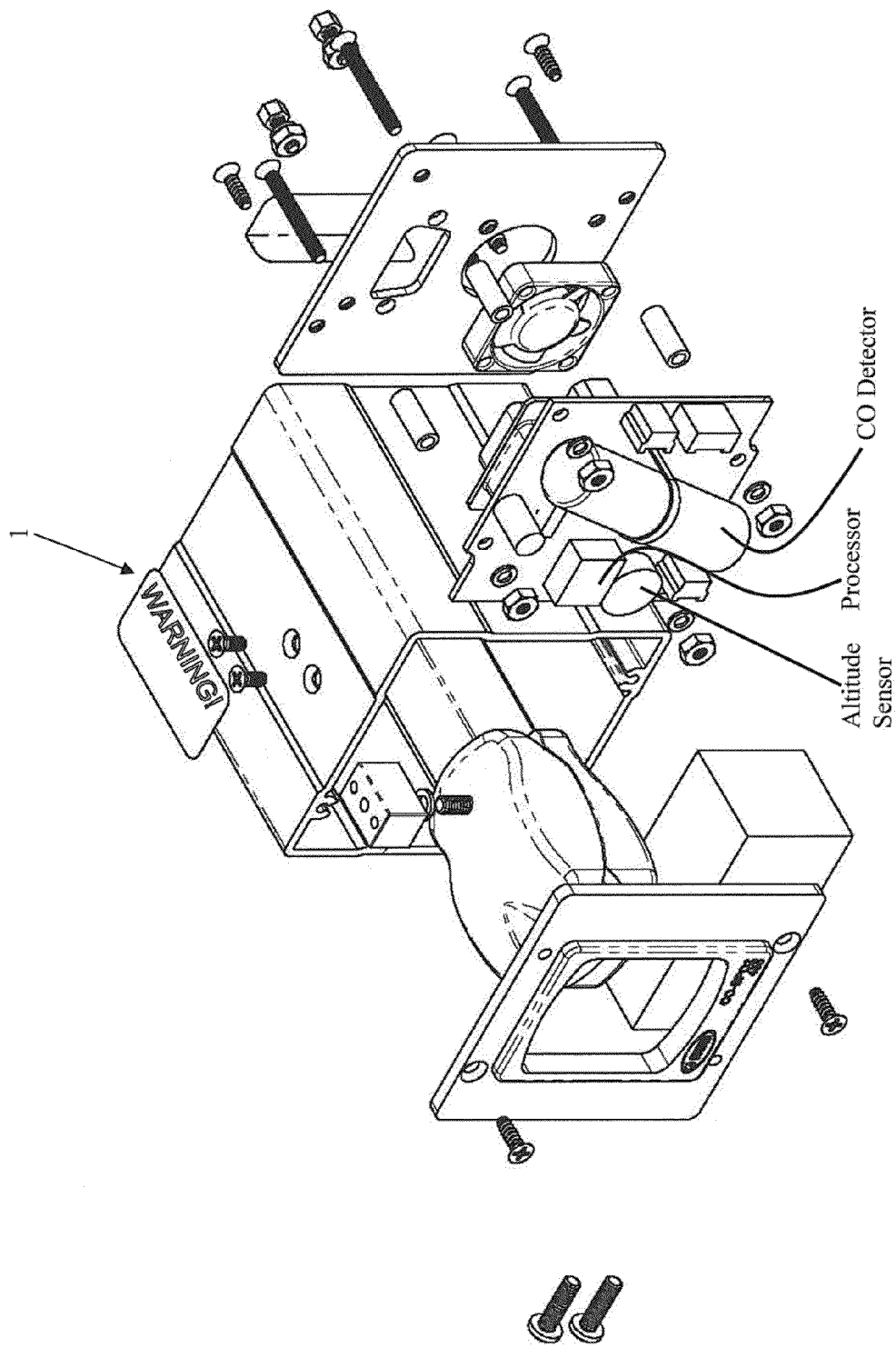

As explained and schematically shown in provisional application Ser. No. 61/221,488 filed Jun. 29, 2009, the housing of the sensor 1 can extend into the area of the aircraft behind the firewall. When the sensor is located in the cockpit, it is in circuit communication with a processor associated with the multifunctional display 20 of the cockpit. The processor associated with the multifunctional display 20 is located in a housing 40 (FIG. 6, Exhibit E) which can be part of or separate from the multifunctional display 20. The multifunctional display 20 is located proximate to a pilot in the aircraft cockpit. As shown in FIG. 6, appropriate circuitry communicates the sensor 1 with the processor associated with the multifunctional display 20. Also, Exhibit E schematically illustrates the manner in which an altitude sensor and CO sensor are integrated into the system. The altitude sensor provides the data as to the altitude of the aircraft, which data is communicated to the processor 40. The processor 40 is configured to determine the time at the sense altitude and to output data that is used to prompt the cockpit occupant to monitor vitals based on the time at the sensed altitude.

Additional features of the system and method of the present invention are:

1) a control box system has a built in wired RS232 port to receive data and/or a wireless receiver (e.g., Bluetooth). The control box system conforms to the aviation standards in place, e.g., some of the current standards are ARINC 429, ARINC 441, AIRINC 708. The data can be received from the occupant (e.g. pulse oximetry from the pilot). The control box system may optionally allow recording of the data (health and/or aircraft cabin conditions (e.g., cabin temperature, cabin pressure, cabin carbon monoxide content, aircraft location from global positioning system). This data may be optionally transmitted and recorded in a portable device carried by the occupant. This transmittal may be wired or wireless. Exhibits B and C show data from the control box that has been transmitted via Standard aircraft communication protocol (RS232, Airinc 429... etc) and presented to the pilot at the Multi Function Display 20.
2) Anytime during a flight, the pilot can put a finger into the pulse oximetry sensor 1 and get a reading on the pilot's oxygen level and heart rate The reading would be shown at the multifunctional display, as shown in FIG. 1. In addition, the instrument panel can have features such as buttons and displays 32, 34, 36, that relate to CO alert signals, aircraft altitude signals, and CO sensing reset signals, in accordance with U.S. patent application Ser. No. 11/288,716, that is incorporated by reference herein.
3) The pulse oximetry sensor component 1a can be of a type produced by Nonin (Plymouth, Minn.) or other manufacturer, and will send data to the control box system associated with the multifunctional display, either thru wire or bluetooth. The control box is shown in provisional application Ser. No. 61/221,488 (incorporated by reference herein).
4) The data is read by the processor and produces output relating to the pilot's vital signs that is displayed to the pilot at the multifunctional display. That data can also be transmitted to a ground station that is monitoring the vital signs of the pilot.
5) The software and other hardware associated with the processor from the control box system is also configured to analyze the cabin altitude produced by CO Guardian (Tucson Ariz.), cabin temperature produced by CO Guardian (Tucson, Ariz.), as well as occupant's vital signs (Heart Rate, occupant temperature, Blood Oxygen pulse oximetry, blood pressure, temperature, glucose level Breath Analyzer) and is configured to transmit alarm to the occupant or a co-occupant via a software if it determines it's appropriate.
6) The system and method can also analyze the cockpit conditions (Altitude, temperature, GPS location) and send a reminder to the pilot to check his vital signs via the RS232 data bus to the cockpit displays in flight. Moreover, the system and method can transmit the data and the times the data was taken, via the Bluetooth to a laptop or other Bluetooth devices for history data.
7) The system and method are preferably configured to provide the following indications:
   i. System failure (includes sensor and the control box system)
   ii. Absence of the occupant's examination target, such as: Finger detection/No finger detected for a pulse oximeter.
   iii. Reminder (which can be displayed on the multifunctional display) to check finger pulse, or an indication that the system failed to provide an intended reminder, or a reminder to take appropriate medication.
   iv. An alarm condition based on the detected health signal.
8) The output of any of these conditions is displayed to the pilot on the multifunctional display, galley display units, passenger service units or PSU (e.g., personnel entertainment systems or overhead console panels), black box, any other recording devices in the aircraft, and can also be transmitted to a ground station. The data from the control box system can also be stored for history analysis.
9) Furthermore, data can be gathered for animals in the cargo area and vital signs transmitted to the Control Box System, then to Multi Function Display control Box and then to Multi Functional Display.
10) Exhibit E shows additional details of the manner in which the sensor 1, the processor 40, the altitude sensor, and the CO detector are assembled and connected with the instrument panel.
11) The sample output from the control box can be the following.
   $PCOG452HR<sp>XFDRAAA.123.123.123.123.123.123.123 <CR><LF>

Where:
$PCOG452HR ASCII characters describe the control unit that is sending data to MFD
<sp> space (0×20) char
X System failure indication "0×31 char: Unit fail", "0×30 char: Unit OK"
F Sensor Failure indication "0×31 char: Unit fail", "0×30 char: Unit OK"
D Finger Detection "0×31 char: Finger Detected", "0×30 char: No Finger Detected"
R Reminder to check finger pulse and SPO2 "0×30 char No reminder", "0×31 char reminder to check"
A Alarm condition 1 "0×30 char No alarm", "0×31 (To be Identified)
A Alarm condition 2 "0×30 char No alarm", "0×31 (To Be Identified)
A Alarm condition 3 "0×30 char No alarm", "0×31 (To be Identified)
. Separator character before heart rate/pulse
123 Heart rate/pulse ASCII-coded decimal format 0×31,0×32, 0×33
. Separator character before oxygen %
123 SPO2 (Oxygen %) ASCII-coded decimal format 0×31, 0×32, 0×33
. Separator character before BP (SYS)
123 Blood Pressure (systolic) ASCII-coded decimal format 0×31,0×32, 0×33
. Separator character before BP (DIA)
123 Blood Pressure (diastolic) ASCII-coded decimal format 0×31,0×32, 0×33
. Separator character before Blood Glucose
123 Blood Glucose (mg/dl) ASCII-coded decimal format 0×31, 0×32, 0×33
. Separator character before body temperature
123 Body Temperature in Celsius ASCII-coded decimal format 0×31,0×32, 0×33
. Separator character before Alcohol Breathalyzer Thus, the present invention provides a system and method by which human vital condition data of a cockpit occupant (e.g. an aircraft pilot) is monitored, and output related to that condition is presented to the pilot (e.g. via the multifunctional display of the aircraft). The sensor 1 is configured to provide data related to at least one human vital condition, and is located within the reach of an occupant of the cockpit. The sensor 1 is in communication with a processor 40 for data from the sensor, and the processor provides the multi functional display 20 with output related to the human vital condition based on the data from the sensor.

The sensor 1 and the multifunctional display 20 communicate, e.g. via a control box system, and the communication can be e.g. a wired connection, a wireless connection, etc. The sensor data is transmitted and/or recorded on the aircraft (aircraft black box or the control box system) or at a ground station.

The sensor 1 is supported by one of an aircraft panel 30 and seat 21, in stabilized condition in an aircraft panel, within reach of an occupant of the cockpit.

During operation of an aircraft, a person seated in the aircraft cockpit seat 21 is reminded to engage the sensor to produce data as to the human vital condition of the cockpit occupant, that is communicated to the processor, and produces output at the multi functional display related to the human vital condition. Thus, if the occupant's vital signs require some attention by the occupant or others on the aircraft, the output at the multifunctional display is designed to get the attention of the occupant or such others. In accordance with an important aspect of this invention, an aircraft pilot will get periodic prompts (via the programming of processor 40) based on the sensed altitude of the aircraft and time at that sensed altitude to monitor the pilot's vitals, and those periodic reminders will be shorter in time as the aircraft altitude increase (for example, at 10,000 feet altitude the pilot can be prompted to monitor vitals every 60 minutes and at 20,000 feet at every 15 minutes). Thus, a pilot who is occupied with a myriad of tasks to perform in flying the aircraft, and who may otherwise be too busy to remind himself/herself to monitor vitals will be periodically prompted to monitor vitals, at an increasing frequency as the altitude of the aircraft increases.

The data from the sensor 1 is also communicated to a storage device (e.g. the aircraft black box), so there is a continuing record of whether the pilot monitored his/her vitals as instructed, and if so what those vitals were when they were monitored. Also, such data may be communicated to a ground station, so that the pilot's vitals can be monitored at the ground station.

The data from the sensor 1 is preferably blood oxygen data, but can also be related to any or all of the following additional human vital conditions: blood alcohol, blood glucose, body temperature, blood pressure. In addition, the system and method of monitoring pilot vitals is preferably combined with CO data produced by a system such as disclosed in applicant's U.S. Pat. No. 7,746,240, which is incorporated by reference herein. Since CO levels can be at dangerous levels even before the pilot's vitals (e.g. blood oxygen will reflect the effect of the CO levels, the system and method are designed such that if CO levels reach a predetermined level an alert signal will be triggered, irrespective of the human vital condition that is being monitored.

Thus, as seen by the foregoing description, the present invention provides a new and useful system and method that is designed to enable an occupant (e.g. a pilot) and/or a ground station to monitor the physical condition of the occupant during a flight. With the principles of the invention in mind, the manner in which those principles can be applied to monitoring the physical condition of various aircraft occupants will become apparent to those in the art.

The invention claimed is:

1. A sensing and reporting system for an aircraft, comprising a display, and a sensor configured to provide data related to at least one human vital condition, within the reach of an occupant of the cockpit, the sensor in communication with a processor for data from the sensor, the processor providing the display with output related to the human vital condition based on the data from the sensor, and means for prompting the cockpit occupant to engage the sensor, wherein the means for prompting the cockpit occupant to engage the sensor is configured to prompt the cockpit occupant based on the sensed altitude of the aircraft and time at that sensed altitude.

2. The system of claim 1, wherein the said display comprises a multifunctional display and the sensor and the said multifunctional display communicate via a control box system.

3. The system of claim 2, wherein the said control box system communicates with the said sensor wirelessly.

4. The system of claim 1, wherein the said display comprises a multifunctional display that is part of an aircraft instrument panel, and wherein the sensor is fixed to one of the instrument aircraft panel and seat.

5. The system of claim 4, wherein the said sensor comprises a pulse oximeter that is supported in a fixed, stabilized position in an aircraft panel, within reach of an occupant of the cockpit.

6. The system of claim 1, wherein the sensor data is transmitted and/or recorded on the aircraft or at a ground station.

7. The system of claim 6, wherein the said data is recorded in at least one of aircraft black box or the said control box system.

8. The system of claim 1, wherein the said control box system communicates with a portable device, and data from the control device is recorded in the portable device.

9. A method comprising
  a. providing a system for an aircraft, comprising a display, and a sensor within the reach of a cockpit occupant, the sensor configured be engaged by a cockpit occupant seated in the cockpit to provide data related to at least one human vital condition, the sensor in communication with a processor for data from the sensor, and the processor providing the display with output related to the human vital condition based on the data from the sensor
  b. prompting a cockpit occupant seated in the cockpit to engage the sensor to produce data as to the human vital condition, that is communicated to the processor, and produces output at the display related to the human vital condition, further including prompting the cockpit occupant by sending a reminder to the cockpit occupant that is designed to remind the cockpit occupant to engage the sensor to produce the data related to the at least one human condition.

10. The method of claim 9, including providing the reminder to the cockpit occupant based on the sensed altitude of the aircraft and time at that sensed altitude.

11. The method of claim 10, further including providing periodic reminders to the cockpit occupant when the sensed altitude of the aircraft is above a predetermined level.

12. The method of claim 11, further including providing the periodic reminders to the cockpit occupant at different time intervals based on the sensed altitude of the aircraft and time at that sensed altitude.

13. The method of claim 12, further including communicating data from the sensor to a storage device.

14. The method of claim 10 further including communicating data from the sensor to a storage device.

15. The method of claim 14, wherein the data from the sensor comprises blood oxygen data.

16. The method of claim 15, wherein the data from the sensor is related to any or all of the following human vital conditions: blood oxygen, blood alcohol, blood glucose, body temperature, blood pressure.

17. The method of 14, further including monitoring the CO level of the aircraft cockpit, and providing an alert signal to the cockpit occupant if the CO level reaches a predetermined level, irrespective of the state of the human vital condition that is displayed on the multifunctional display.

* * * * *